United States Patent [19]

Barnard et al.

[11] 4,268,173

[45] May 19, 1981

[54] REFLECTOMETERS

[75] Inventors: William R. Barnard, Horsham; Phillip W. Francis, Crawley Down, both of England

[73] Assignee: Direct Power Limited, London, England

[21] Appl. No.: 970,117

[22] Filed: Dec. 18, 1978

[30] Foreign Application Priority Data

Dec. 22, 1977 [GB] United Kingdom ............... 53606/77
Mar. 15, 1978 [GB] United Kingdom ............... 10283/78

[51] Int. Cl.³ .......................................... G01N 21/55
[52] U.S. Cl. ..................................... 356/445; 392/244
[58] Field of Search ............... 356/443, 444, 445, 446, 356/447, 448, 244, 36

[56] References Cited

U.S. PATENT DOCUMENTS 3,528,749 9/1970 Bowker ................................ 356/443
3,600,099 8/1971 Schoeffel ............................ 356/448
3,999,948 12/1976 Deindoerfer et al. ............... 356/244
4,040,747 8/1977 Webster ............................. 356/244

Primary Examiner—R. A. Rosenberger
Attorney, Agent, or Firm—Schwartz & Weinrieb

[57] ABSTRACT

An optical reflectometer includes an optical head having a measuring chamber defined therein and a measuring zone defined within the chamber. A pair of non-parallel bores are defined within the front wall of the head and optically lead into the measuring chamber so as to intersect at the measuring zone. A light source is optically associated with one of the bores while a photodetector is optically associated with the other one of the bores. A carrier, having a cut-away section defined within its front wall for accommodating the light path defined by the light source, the measuring zone, and the photodetector, is removably disposed within the optical head and serves to carry, and position, a test object with respect to the measuring zone, the object, in turn, being removably disposed within the carrier.

13 Claims, 3 Drawing Figures

REFLECTOMETERS

FIELD OF THE INVENTION

This invention is concerned with reflectometers, and in particular with a simple optical reflectometer which can be used, for example, to determine the glucose content of a blood sample.

BACKGROUND OF THE INVENTION

The normal concentration of glucose in the body is 3-7 millimoles per liter, and unless the concentration is regulated to within this normal range, there can be long term complications in the body leading for example to blindness.

For non-diabetics, this regulation is controlled automatically by an enzyme in the body. Diabetics, on the other hand, lack this enzyme and must therefore resort to use of a carefully controlled diet or, in some cases, the use of insulin injections.

Reflectometers have already been developed to determine the glucose content of a blood sample. The sample is taken and transferred to a test stick containing reagents including an enzyme which, indirectly, reacts with the glucose of the blood to change the colour of a dye. The greater the glucose content, the deeper becomes the colour of the dye. After a fixed period, the bood is washed or wiped off the test stick, and the stick is inserted into the reflectometer to provide a reading dependent on the colour of the dye.

Sophisticated reflectometers which include glass components such as prisms and mirrors would be too expensive for this type of application where accuracy need not be greater than about ±0.5 millimoles per liter. Attempts to produce a simple, inexpensive reflectometer have therefore been made. However, these meters are still rather bulky and difficult to use and are not therefore suitable for use by a diabetic at home. For example, one such meter requires a two-stage calibration each time the meter is used. It also relies upon the movement of a pointer over a graduated non-linear scale to provide its readout. Moreover, the test stick is inserted in a hinged cover which, as it closes, trips a microswitch to switch on the meter, and we have found that different readings can be obtained for the same sample depending on the point at which the cover is pressed to trip the microswitch. A need therefore exists for a more convenient and reliable meter.

SUMMARY OF THE INVENTION

In accordance with one aspect of the present invention there is provided an optical reflectometer comprising means defining an incident light path, means for guiding a test object along a fixed path intercepting the incident light path, and photoresponsive means positioned to receive light reflected from an object located at the intersection of the two said paths. Preferably the fixed path lies substantially normal to a plane containing both the incident and reflected light paths.

The guiding means preferably includes the carrier for the object and a chamber for receiving a carrier, an opening in a front wall of the chamber being aligned with an opening in a front wall of the carrier when the carrier is located in the chamber. In one embodiment of the invention the object is then moved along the fixed path by first locating the object in the carrier and then inserting the carrier into the chamber. In an alternative embodiment, the object is moved along the fixed path by first inserting the carrier into the chamber and then locating the object in the carrier.

Either of these arrangements ensures that the object is consistently located at substantially the same distance from the light source when a measurement is made even if the carrier is used as an actuating device to trip the measuring circuit.

Since diabetics tend to have poor eyesight, the meter preferably includes a digital display readout instead of moving a pointer over a graduated scale. However in cases where the output voltage of the photocell (which is proportional to the depth of colour in the sample being tested) has a substantially logarithmic relationship with the parameter being measured (such as the glucose content of a blood sample), the use of a digital display (which is inherently linear) means that the meter must include a logarithmic converter. Known converters of this type usually include computers and/or function generators and would therefore add considerably to the cost of the meter.

In accordance with a further aspect of the present invention such a logarithmic converter comprises a RC network, means for initially charging the capacitance of the network to a predetermined voltage exceeding that of the output voltage being measured, means for discharging the capacitance to provide a logarithmically decaying reference voltage, and means for measuring the period required for the reference voltage to fall to the level of the output voltage.

Preferably the measuring means includes a pulse generator, a counter for counting the generated pulses, a comparator for comparing the two voltages, means for energising the counter at the start of the comparison, and means responsive to the output of the comparator for inhibiting the pulse generator when the reference voltage has fallen to the level of the output voltage. The counter thus provides a digital read-out of the basic parameter represented by the output voltage.

BRIEF DESCRIPTION OF THE DRAWINGS

For a better understanding of the invention one example of a meter embodying the invention will now be described with reference to the accompanying drawings in which.

DETALED DESCRIPTION OF THE PREFERRED EMBODIMENTS

Figure 1:
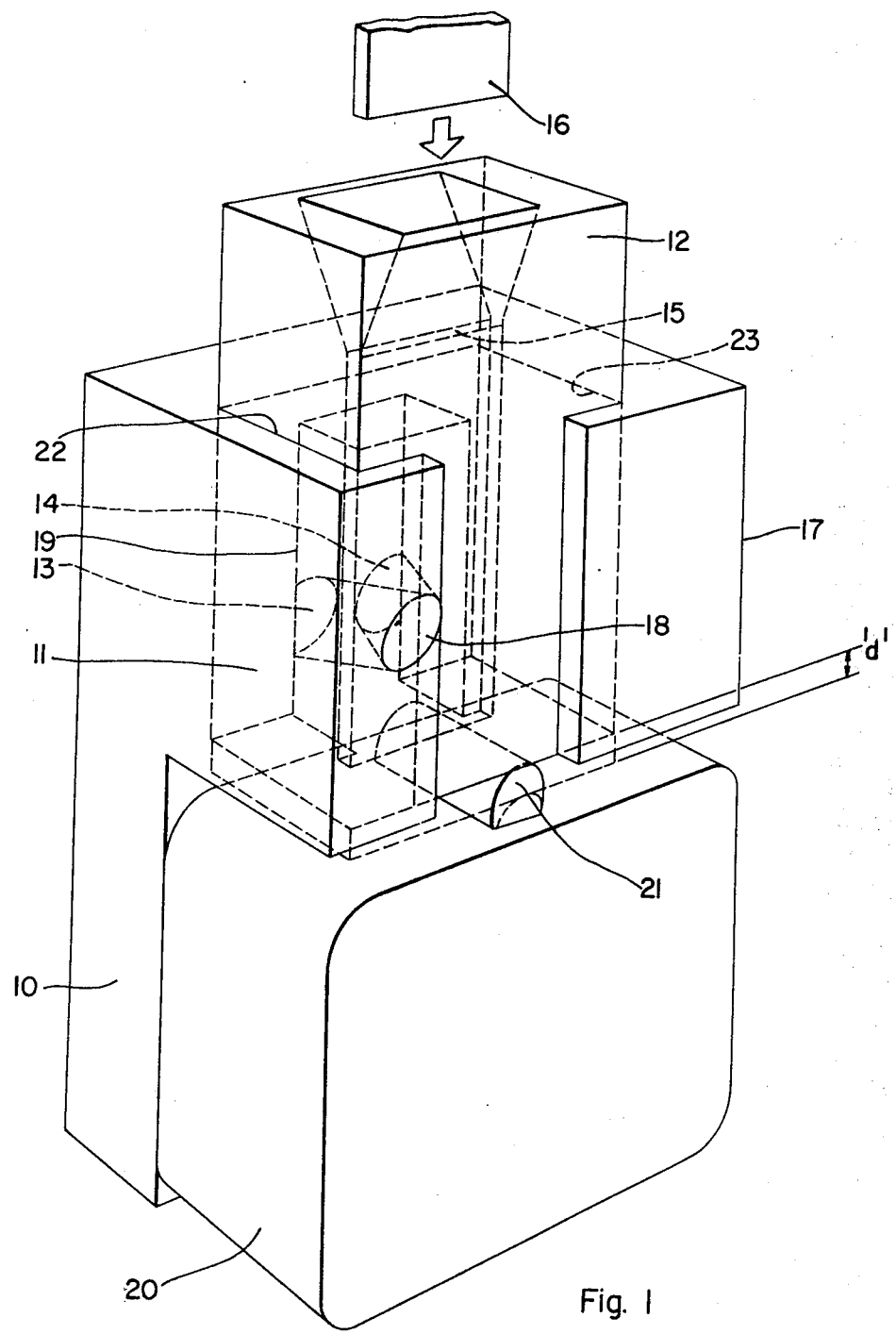
FIG. 1 is a perspective view of an optical head for use in a reflectometer which measures the glucose content of a blood sample

Referring first to FIG. 1, the illustrated optical head includes an opaque front wall 10 and half-length side walls 11 and 17. The front wall 10 includes a pair of openings 13 and 14 extending along paths which intersect one another at a measuring zone 18 lying within the measuring chamber defined by the walls 10, 11 and 17.

A light emitting diode (not shown) directs light through the opening 14 and this light is reflected from the measuring zone through opening 13 to a photodetector (not shown).

In use, a test stick 16 (consisting of a firm plastic strip carrying an impregnated area containing reagents which react with the glucose in a blood sample) is treated with a blood sample for a standard time period, and is then inserted into a slot 15 formed in a carrier 12, the carrier itself being slidably mounted in recessed portions 22 and 23 formed in the respective side walls of the head. The front face of the carrier 12 (i.e. the face which receives the incident light) includes a cut-away portion 19 so that, with the carrier fully inserted, the impregnated portion of the test stick is exposed to the incident light in the measuring zone 18.

Beneath the upper projecting portion of the head is a microswitch 20 having an actuating button 21. Once inserted, the carrier 12 is normally rests on this button 21 but when the carrier is depressed through the distance 'd', the microswitch is tripped. The location of the microswitch is not critical provided that it can be actuated in response to insertion of the carrier into the head.

In one alternative embodiment, the lower portion of the slot 15 includes an integrally moulded leaf spring which accurately positions the test stick in the slot by eliminating any clearance between the stick and the walls of the slot. To further improve the accuracy with which the stick is positioned relative to the photo-detector, the carrier 12 may be tapered so that it is precisely wedged in the measuring chamber. In this case the carrier is not used to actuate the microswitch, and the carrier remains permanently located in the optical head except when removed for cleaning. A separate keyboard switch remote from the optical system is then manually operated to trip the measuring circuit as soon as the stick has been inserted into the carrier.

When using an infra-red light emitting diode as the light source, a suitable colour filter is preferably inserted in the light path to mask the effect of blood corpuscles which may remain on the test stick after the blood has been washed or wiped off.

Figure 2:
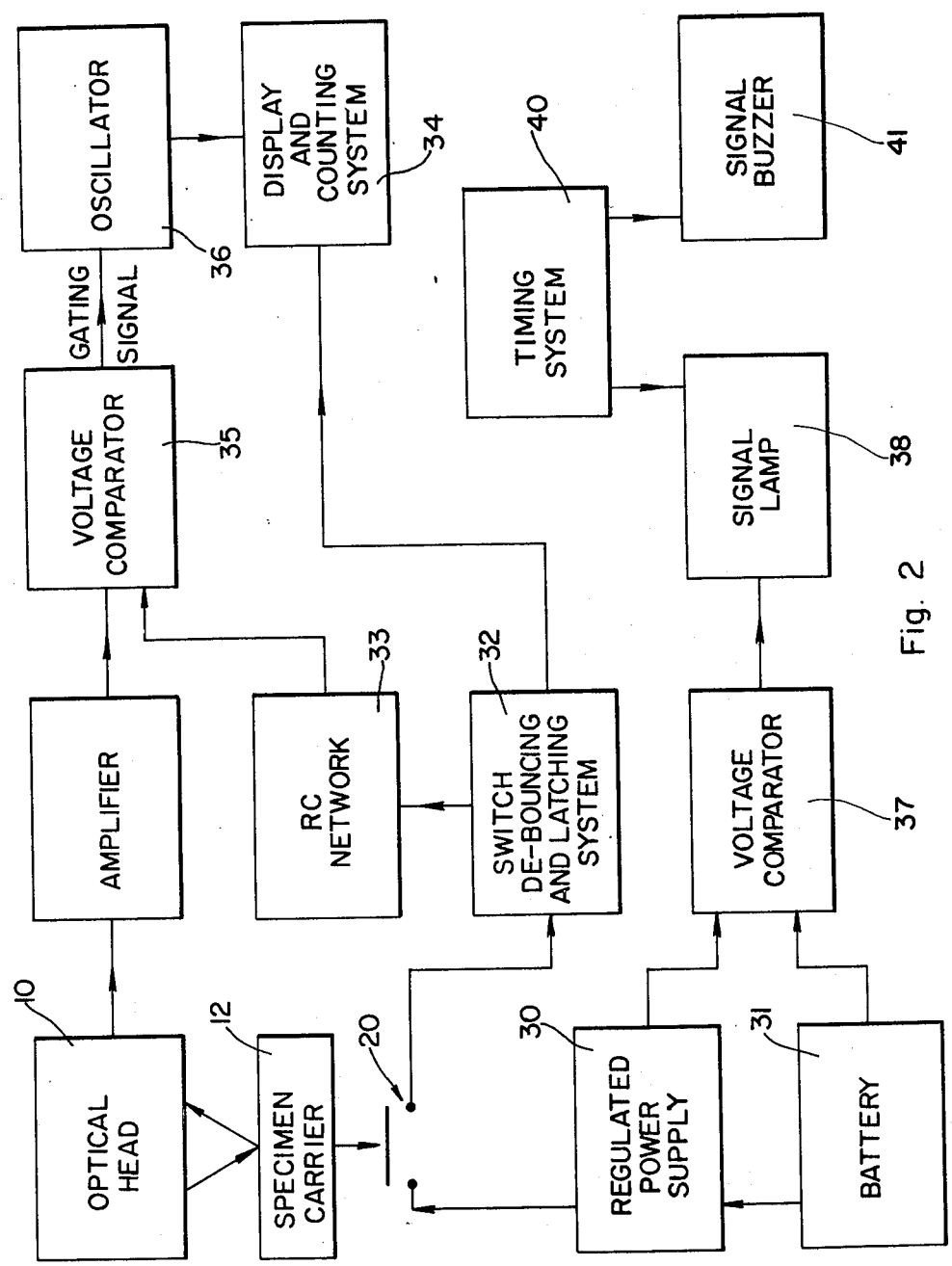
FIG. 2 is a block circuit diagram of the meter.

Referring next to FIG. 2, the optical head 10, the sample carrier 12, and the microswitch 20 are again identified by the same reference numerals.

When the switch 20 is tripped, a regulated power supply 30 fed from a battery 31 is connected to a switch debouncing and latching system 32. This cuts off the supply voltage to an RC network 33 and also starts a display and counting system 34. The logarithmically decaying voltage thus obtained from the RC network 33 is fed to one input of a voltage comparator 35, and the other input of the comparator receives an amplified signal from the photodetector associated with the optical head 10.

When the RC voltage has fallen to the same level as the signal voltage, the comparator will change state. Since the RC volts-time relationship is logarithmic, the time period from the moment the switch 20 is tripped to the comparator change of state will be a logarithmic function of the difference between the original RC voltage and the ouput from the photocell.

An oscillator 36 is switched off when the output of the comparator changes state. The count displayed on the counter and display system 34 is thus proportional to the time it takes for the RC voltage to drop to the signal voltage. This time has an inverse logarithmic relationship with the output voltage and, since the output voltage has a logarithmic relationship with the blood glucose content, the time (and therefore the count) has a linear relationship with blood glucose content. A logarithmic to linear conversion is thus achieved and, by suitably setting up the RC voltage and the oscillator frequency, the count displayed can be made to correspond to the blood glucose content.

Another voltage comparator 37 monitors the output of the regulated power supply and provides an output whenever the voltage falls below a certain level. At this point a signal lamp 38 is lit to indicate that the battery 31 requires recharging.

When a blood sample is initially placed on the test stick, it reacts with an enzyme which, indirectly, produces a change of colour in a dye. This change of colour is dependent on the time for which the blood sample is in contact with the stick. Accordingly, it is important that the blood should be washed or wiped off after a fixed, standard time period. To provide an indication of this reaction period, the present meter incorporates a timer 40 which starts timing immediately the instrument is switched on. A few seconds before the end of the reaction period, a buzzer 41 is sounded and the signal lamp is illuminated. When the buzzer and the lamp go off, the reaction period is completed.

Figure 3:
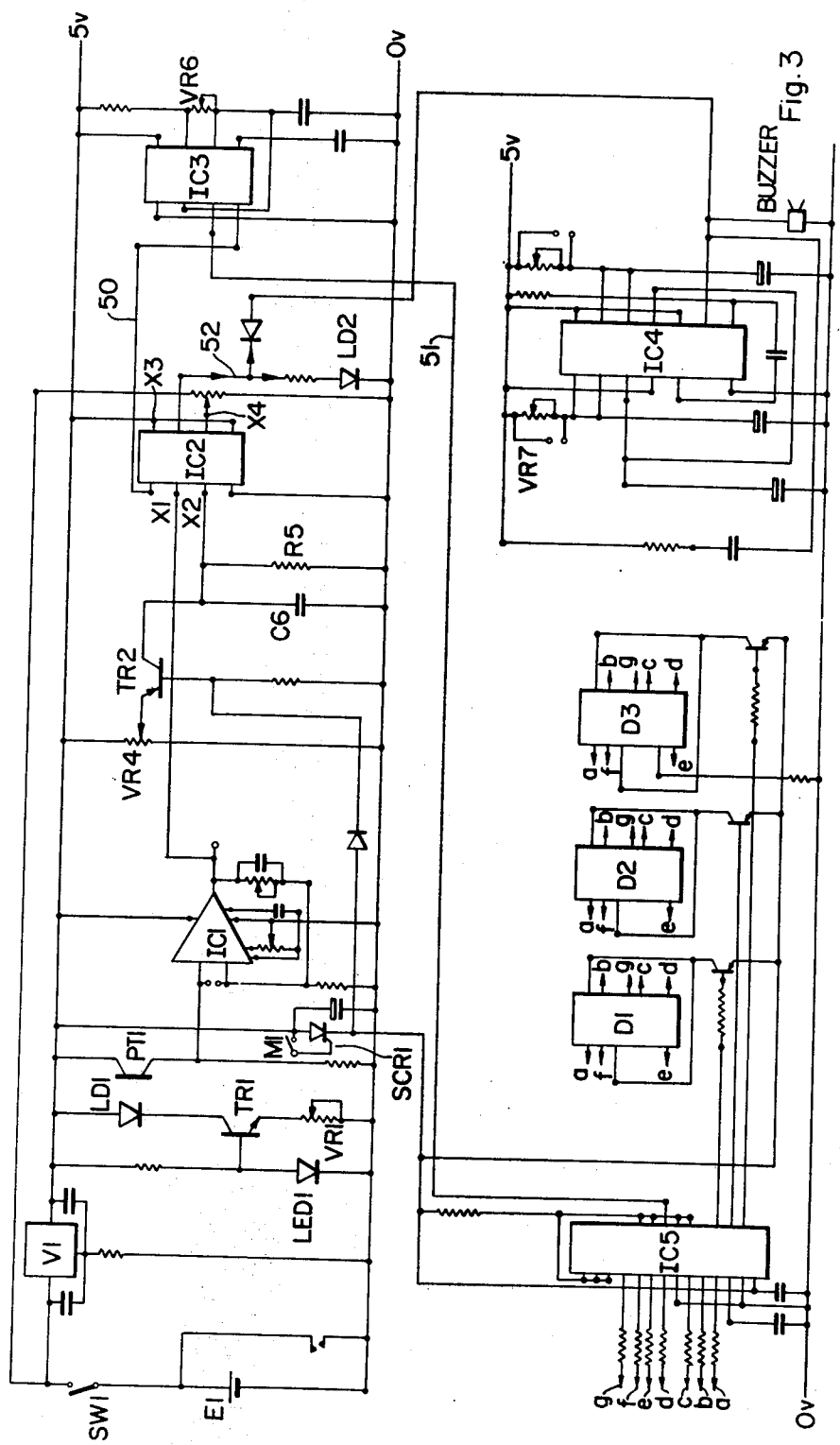
FIG. 3 is a complete circuit diagram of the block circuit shown in FIG. 2.

Referring now to the circuit diagram of FIG. 3, the meter is switched on by closing switch SW1. This connects a 6 volt rechargeable battery E1 to a 5 volt regulated power supply V1, and this energises a light emitting diode LD1 through a transistor TR1 and a variable register VR1. It also biases "ON" a transistor TR2 so that a capacitor C6 is charged to a voltage dependent on the setting of a variable resistor VR4, and it switches on an oscillator IC3.

As previously explained, the light from the light emitting diode is reflected from the test sample to a photocell. The photocell comprises a phototransistor PT1, and the resulting voltage at the emitter of the transistor is amplified by the amplifier IC1 before being fed to the input X1 of a comparator chip IC2. A second input X2 of the comparator IC2 receives a voltage from the RC network consisting of a capacitor C6 and a resistor R5.

A measurement is made when a microswitch M1 is tripped. This switch corresponds to the switch 20 shown in FIGS. 1 and 2. Closure of switch M1 fires a silicon controlled rectifier SCR1 so that the supply voltage is fed both to the display and counting system (consisting of a counter IC5 and display units D1, D2 and D3) and also to the base of transistor TR2 via a diode. The transistor TR2 is thus biased "OFF" and the capacitor C6 discharges through resistor R5 to provide the logarithmically decaying reference voltage at input X2 of the comparator IC2.

At the start of the comparison, the oscillator IC3 begins supplying pulses to the counter IC5 along line 51. When the voltage at the input X2 falls to the level of the voltage at the input X1, the output from IC2 on line 50 changes state and this biases the oscillator IC3 "OFF". Thus the number of pulses counted by the counter IC5 provides a measure of the period required for the voltage at X2 to fall to the level of the voltage at X1. The frequency of the oscillator can be adjusted by means of the variable resistance VR6.

The comparator chip IC2 includes a second comparison circuit which compares the voltages at the inputs X3,X4 to provide a comparison of the battery voltage E1 with the regulated supply voltage from the power supply V1. The result of this comparison is fed along line 52 to a light emitting diode LD2 so that the diode is energised whenever the regulated voltage falls below a predetermined level.

A timer circuit IC4 also responsive to the output on line 52 provides an output to the buzzer B1 as explained in connection with the block diagram of FIG. 2.

Obviously, many modifications and variations of the present invention are possible in light of the above teachings. It is therefore to be understood that within the scope of the appended claims, the invention may be practiced otherwise than as specifically described herein.

We claim

1. An optical reflectometer, comprising:
   means, including at least a front wall, for defining a chamber;
   means defining an incident light path extending from said front wall of said chamber-defining-means to said chamber;
   carrier means, removably disposed within said chamber and having means for accommodating said incident light path defined within said chamber-defining-means, for removably guiding a test object relative to said carrier means and for carrying said test object, along a fixed path intercepting said incident light path, to a fixed position located within said incident light path; and
   photoresponsive means for receiving light reflected from said test object.

2. An optical reflectometer as set forth in claim 1, wherein:
   said front wall further includes means for defining a reflected light path for transmitting said reflected light from said test object to said photoresponsive means.

3. An optical reflectometer as set forth in claim 1, wherein:
   said means defining said chamber further comprises two opposing sidewalls extending rearwardly from said front wall, said two sidewalls being recessed so as to define a channel for slideably receiving said carrier means.

4. An optical reflectometer as set forth in claim 1, wherein:
   the front face of said carrier means abuts the rear face of said front wall of said means defining said chamber.

5. An optical reflectometer as set forth in claim 1, wherein:
   said carrier means comprises a substantially rectangularly shaped block having slot means defined therein for slideably receiving said test object in the form of a flat strip.

6. An optical reflectometer as set forth in claim 5, wherein:
   said block is tapered so as to positively locate said block within said chamber-defining-means.

7. An optical reflectometer as set forth in claim 5, wherein:
   said slot means includes a resilient protuberance for locating said test object therein substantially without any clearance between said test object and the walls of said slot means.

8. An optical reflectometer as set forth in claim 1, wherein:
   a solid state light source provides said incident light.

9. An optical reflectometer as set forth in claim 8, wherein:
   said solid state light source comprises a light emitting diode.

10. An optical reflectometer as set forth in claim 1, further comprising:
    color filter means disposed within said incident light path.

11. An optical reflectometer as set forth in claim 1, wherein:
    said fixed path lies substantially perpendicular to a plane containing both said incident and reflected light.

12. An optical reflectometer as set forth in claim 1, wherein:
    said means defining said incident light path comprises a bore defined within said front wall of said chamber-defining-means; and
    said means for accommodating said incident light path comprises a cut-away portion defining an aperture within said carrier means.

13. An optical reflectometer, comprising:
    means for defining a chamber and including a front wall and a pair of opposed sidewalls extending rearwardly from said front wall;
    first means defining an incident light path extending from said front wall of said chamber-defining-means to said chamber;
    carrier means, removably disposed within said chamber behind said front wall and between said opposed sidewalls and having means for accommodating said incident light path defined within said chamber-defining means, and having slot means defined therein for removably guiding a test object relative to said carrier means and for carrying said test object, along a fixed path intercepting said incident light path, to a fixed position located within said incident light path;
    second means defining a reflected light path extending from said chamber to said front wall of said chamber-defining-means; and
    photoresponsive means disposed outside of said chamber for receiving reflected light from said test object along said reflected light path.

* * * * *